United States Patent [19]

Cairns et al.

[11] Patent Number: 4,474,787
[45] Date of Patent: Oct. 2, 1984

[54] 7,6 DIOXO-4H,6H-PYRANO[3,2-g]QUINOLINE DICARBOXYLIC ACIDS AND ANTI-ALLERGIC USE THEREOF

[75] Inventors: Hugh Cairns; David Cox, both of Loughborough, England

[73] Assignee: Fisons Limited, England

[21] Appl. No.: 344,982

[22] Filed: Feb. 2, 1982

Related U.S. Application Data

[63] Continuation of Ser. No. 946,492, Sep. 28, 1978, abandoned, which is a continuation-in-part of Ser. No. 897,416, Apr. 18, 1978, abandoned.

[30] Foreign Application Priority Data

May 4, 1977 [GB] United Kingdom .............. 18597/77
Nov. 4, 1977 [GB] United Kingdom .............. 48565/77
Apr. 25, 1978 [GB] United Kingdom .............. 16168/78

[51] Int. Cl.³ .................... A61K 31/47; C07D 491/04
[52] U.S. Cl. ...................................... 424/258; 546/89; 546/92
[58] Field of Search ...................... 546/89, 92; 424/258

[56] References Cited

U.S. PATENT DOCUMENTS 3,773,769 11/1973 Albrecht et al. ........................ 546/89
4,117,134 9/1978 Connor et al. ......................... 546/92

FOREIGN PATENT DOCUMENTS 073427 3/1975 Japan ..................................... 546/89

Primary Examiner—Glennon H. Hollrah
Assistant Examiner—D. B. Springer
Attorney, Agent, or Firm—Marshall, O'Toole, Gerstein, Murray & Bicknell

[57] ABSTRACT

There are described compounds of formula I

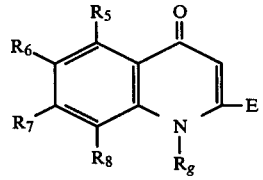

in which an adjacent pair of $R_5$, $R_6$, $R_7$ and $R_8$ form a chain —COCH=CE—O—, and the remainder of $R_5$, $R_6$, $R_7$ and $R_8$, which may be the same or different, each represent hydrogen, hydroxy, alkyl, halogen, alkenyl, alkoxy, or —$NR_1R_2$ in which $R_1$ and $R_2$, which are the same or different, are each hydrogen or alkyl, $R_g$ is hydrogen, alkyl, alkenyl or phenyl-alkyl, and
E is —COOH, a 5-tetrazolyl group or an (N-tetrazol-5-yl) carboxamido group, and pharmaceutically acceptable derivatives thereof.

There are also described processes for making the compounds and pharmaceutical, e.g. anti-allergic, compositions containing the compounds.

11 Claims, No Drawings

7,6 DIOXO-4H,6H-PYRANO[3,2-G]QUINOLINE DICARBOXYLIC ACIDS AND ANTI-ALLERGIC USE THEREOF

This is a continuation of application Ser. No. 946,492, filed Sept. 28, 1978 abandoned which is a CIP of Ser. No. 897,416 filed Apr. 18, 1978 abandoned.

This invention relates to new pyranoquinolinone derivatives, compositions containing them and methods for their preparation.

According to our invention we provide compounds of formula I,

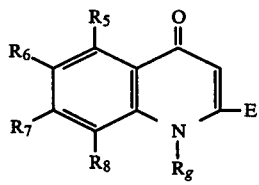

in which an adjacent pair of $R_5$, $R_6$, $R_7$ and $R_8$ form a chain —COCH=CE—O—, and the remainder of $R_5$, $R_6$, $R_7$ and $R_8$, which may be the same or different, each represent hydrogen, hydroxy, alkyl, halogen, alkenyl, alkoxy, or —$NR_1R_2$ in which $R_1$ and $R_2$, which are the same or different, are each hydrogen or alkyl, Rg is hydrogen, alkyl, alkenyl or phenyl-alkyl, and
E is —COOH, a 5-tetrazolyl group or an (N-tetrazol-5-yl)carboxamido group,
and pharmaceutically acceptable derivatives thereof.

According to our invention we also provide a process for the production of a compound of formula I, or a pharmaceutically acceptable derivative thereof, which comprises, (a) producing a compound of formula I in which E is —COOH by selectively hydrolysing or oxidising a compound of formula II,

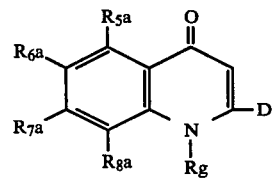

in which Rg is as defined above,
$R_{5a}$, $R_{6a}$, $R_{7a}$ and $R_{8a}$ have the same significances as $R_5$, $R_6$, $R_7$ and $R_8$ above, save than an adjacent pair of $R_{5a}$, $R_{6a}$, $R_{7a}$ and $R_{8a}$ may represent a chain of formula —COCH=C($D_1$)O—, and
one or both of D and $D_1$ represents a group hydrolysable or oxidisable to a —COOH group, and the other may represent a —COOH group, (b) producing a compound of formula I in which E is —COOH by cyclising a compound of formula III or IV,

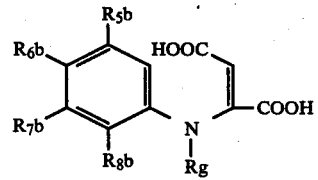

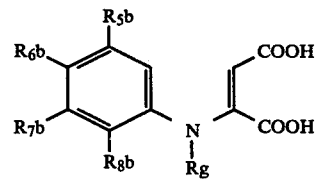

or an ester of either thereof,
in which Rg is as defined above,
$R_{5b}$, $R_{6b}$, $R_{7b}$ and $R_{8b}$ have the same significances as $R_5$, $R_6$, $R_7$ and $R_8$ above, save that an adjacent pair of $R_{5b}$, $R_{6b}$, $R_{7b}$ and $R_{8b}$ may represent the pair of groups —H and —O—C(COOH)=CH—COOH, (c) producing a compound of formula I in which E is —COOH by cyclising a compound of formula V,

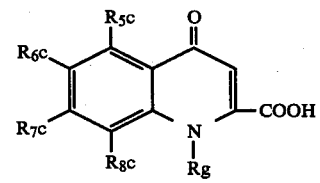

or an ester thereof,
in which Rg is as defined above,
$R_{5c}$, $R_{6c}$, $R_{7c}$ and $R_{8c}$ have the same significances as $R_5$, $R_6$, $R_7$ and $R_8$ above save that an adjacent pair of $R_{5c}$, $R_{6c}$, $R_{7c}$ and $R_{8c}$, instead of forming a chain —COCH=C(COOH)—O—, represent the pairs of groups:

(i) —COCH$_2$CO—COR'' or —COCH=C(COOH)—NL$_1$L$_2$, or a suitable derivative thereof; and —OM or a halogen atom, or
(ii) —H and —O—C(COR'')=CH—COR''

R'' represents —OM, or a group which is hydrolysable thereto,
$L_1$ and $L_2$ which may be the same or different are each hydrogen, aryl or alkyl, or together form a saturated or unsaturated alkylene chain, and
M represents hydrogen or an alkali metal, and if necessary or desired hydrolysing the group —COR'', to a group —COOM, (d) conversion of a compound of formula VI,

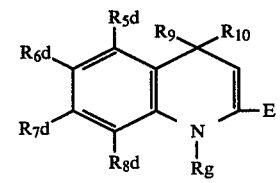

or an ester thereof,
in which Rg and E are as defined above,
$R_{5d}$, $R_{6d}$, $R_{7d}$ and $R_{8d}$ have the same significances as $R_5$, $R_6$, $R_7$ and $R_8$ above save that an adjacent pair of R$_5$d, R$_6$d, R$_7$d and R$_8$d may represent the chain —C(R$_9$R$_{10}$)=CE—O—, at least one of the pairs of groups R$_9$ and R$_{10}$ together form a =S or together form an —S(CH$_2$)$_n$S— chain in which n is 2 or 3, and the other pair R$_9$, R$_{10}$ may represent =O, to a corresponding compound of formula I, (e) selectively removing the groups A and B from a compound of formula VII,

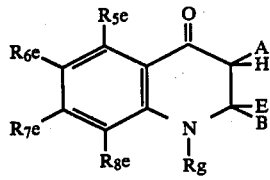

VII or an ester thereof, in which Rg and E are as defined above,

R$_5$e, R$_6$e, R$_7$e and R$_8$e have the same significances as R$_5$, R$_6$, R$_7$ and R$_8$ above save that an adjacent pair of R$_5$e, R$_6$e, R$_7$e and R$_8$e may represent a chain —COCHA—CBE—O—, in at least one of the pairs of groups A and B both A and B are hydrogen, or one of A and B is hydrogen and the other is halogen or hydroxy, and the other pair A, B may together form a double bond, (f) producing a compound of formula I in which E is —COOH by cyclising a compound of formula VIII,

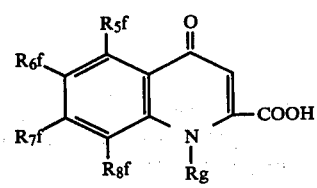

VIII or an ester thereof, in which Rg is as defined above, R$_5$f, R$_6$f, R$_7$f and R$_8$f have the same significances as R$_5$, R$_6$, R$_7$ and R$_8$ above save that an adjacent pair of R$_5$f, R$_6$f, R$_7$f and R$_8$f, instead of forming a chain —COCH=C(COOH)—O—, represent the pair of groups —COCH(SOR$_{10}$)—CH(CH)—COOR" and —OM, R" and M are as defined above, and R$_{10}$ represents an alkyl C 1 to 10 group, (g) producing a compound of formula I in which E is a 5-tetrazolyl group by reacting a corresponding compound of formula I in which E is —CN, with an azide in a solvent which is inert under the reaction conditions, or (h) producing a compound of formula I in which E is an (N-tetrazol-5-yl)carboxamido group by reacting a corresponding compound of formula I in which E is —COOH, or an acid halide, ester or mixed anhydride thereof, with 5-aminotetrazole, and if necessary or desired hydrolysing the ester of the compound of formula I and/or converting the compound of formula I to a pharmaceutically acceptable derivative thereof.

In process (a) the group D may be, for example an ester, acid halide, amide or a nitrile group, which may be hydrolysed to a —COOH group. The hydrolysis may be carried out using conventional techniques, for example under mildly basic conditions, e.g. using sodium carbonate, sodium hydroxide, sodium bicarbonate, or under acidic conditions, e.g. a mixture of aqueous dioxan and hydrochloric acid, or hydrogen bromide in acetic acid. The hydrolysis may be carried out at a temperature of from about 25° to 120° C. depending on the compounds used. Alternatively the group D may be an alkyl, e.g. a lower alkyl such as methyl, a hydroxymethyl, an aralkenyl, e.g. styryl, an acyl, e.g. a lower alkanoyl such as acetyl, or a formyl group. The oxidation may be carried out using conventional techniques which do not otherwise modify the molecule to such an extent that the yield of the desired product is uneconomical, for example an alkyl or a hydroxymethyl group may be oxidised using selenium dioxide, e.g. under reflux in aqueous dioxan; or chromic acid, e.g. under reflux in aqueous acetic acid. Aralkenyl groups may be oxidised using, for example neutral or alkaline potassium permanganate in aqueous ethanol, and acyl groups may be oxidised using, for example chromic acid or an aqueous hypochlorite, e.g. sodium hypochlorite. The formyl group may be oxidised using, for example chromic acid or silver oxide.

In process (b) the cyclisation may be carried out by treating the compound of formula III or IV, with a cyclising agent, for example a dehydrating agent such as chlorosulphonic, sulphuric or polyphosphoric acid. The reaction is preferably carried out under anhydrous conditions and may be carried out at a temperature of from about 25° to 150°, and preferably from 75° to 150° C. We have found that isomerisation of the maleic acid derivative of formula IV to the corresponding fumaric acid derivative of formula III takes place when polyphosphoric acid is used to cyclise these compounds to a compound of formula I, thus enabling a satisfactory yield of the compound of formula I to be obtained from a *prima facie* unsatisfactory mixture of compounds of formulae III and IV. Compounds of formula III may also be cyclised by subjecting the compound to an elevated temperature, e.g. of from 200° to 250° C., optionally in the presence of a high boiling solvent which is inert under the reaction conditions, e.g. diphenyl ether.

When one of the groups is —OM the cyclisation of process (c)(i) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR" is preferably an ester group, e.g. R" may be a lower alkoxy group. When one of the groups is —COCH=C(COOH)—NL$_1$L$_2$ the derivative of the —COOH group may be a group —CONL$_1$L$_2$ in which L$_1$ and L$_2$ are as defined above. It is preferred that L$_1$ and L$_2$ are hydrogen, phenyl, alkyl C 1 to 6 or together form a 4 or 5 membered alkylene chain, e.g. together with the nitrogen atom form a piperidine ring. When one of the groups is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal hydride, e.g. sodium hydride. The reaction is preferably carried out at a temperature of from about 80° to 200° C., in the absence of free oxygen, e.g. under an inert atmosphere such as nitrogen.

The cyclisation of process (c)(ii) may be carried out by treating the compound of formula V with a cyclising agent, for example a dehydrating agent such as chlorosulphonic, polyphosphoric or sulphuric acid. The reaction is preferably carried out under anhydrous conditions and may be carried out at a temperature of from 0° to 100° C. Alternatively cyclisation may be achieved by converting the free carboxy groups of the compound of formula V to acyl halide groups and subjecting the resulting acyl halide to an intramolecular Friedel-Crafts reaction.

In processes (d), when $R_9$ and $R_{10}$ together form a chain $-S-(CH_2)_n-S-$, the conversion may comprise oxidative hydrolysis and may be carried out in an aqueous polar organic solvent, for example aqueous ethanol, acetone or tetrahydrofuran. The oxidative hydrolysis may be carried out in the presence of an oxidising agent, for example mercuric chloride, an N-halosuccinimide such as N-bromo- or N-chloro-succinimide, a per-acid such as periodic acid; or p-toluenesulphonchloramide or a salt thereof. When mercuric chloride is used the reaction may be carried out in the presence of a base, e.g. mercuric oxide, cadmium carbonate or calcium carbonate. N-halosuccinimides may be used alone or in the presence of a silver salt, e.g. silver perchlorate, or silver nitrate. The reaction may conveniently be carried out at a temperature of from about 15° to 100° C.

When $R_9$ and $R_{10}$ together form a $=S$ group the conversion may comprise (oxidative) hydrolysis and may be carried out in the presence of a heavy metal compound, e.g. a compound of group Ib, IIb or IIIb of the Periodic Table of Mendeleef, as catalyst. Suitable compounds include mercury, thallium and silver compounds, e.g. mercury (II) acetate or chloride, thallium (III) trifluoroacetate, or silver oxide. The reaction may be carried out in the presence of water an an organic solvent system such as acetone-acetic acid, alkanols, tetrahydrofuran/methanol, or tetrahydrofuran. Alternatively the reaction may be carried out by alkylation followed by hydrolysis. In such cases the reaction may be effected by (i) an alkyl halide or sulphonate (e.g. methyl iodide), in a moist solvent, e.g. acetone, (II) an alkylfluorosulphonate and water in sulphur dioxide, or (iii) a trialkyl oxonium fluoroborate followed by aqueous sodium hydroxide.

When both A and B are hydrogen process (e) is a dehydrogenation and may be carried out by oxidation using a mild oxidising agent, for example selenium dioxide, palladium black, chloranil, lead tetraacetate or triphenyl methyl perchlorate. Alternatively the dehydrogenation of a compound of formula VII in which both A and B are hydrogen may be carried out indirectly by halogenation followed by dehydrohalogenation, e.g. by treatment with N-bromosuccinimide or pyridinium bromide perbromide to yield a compound of formula VII in which A is halogen and B is hydrogen, which is subsequently dehydrobrominated. When one of A and B is hydroxy the dehydration may be catalysed by an acid, e.g. sulphuric or oxalic acid; a base, e.g. potassium hydroxide; or a salt, e.g. potassium hydrogen sulphate; or N-bromosuccinimide. The reaction may be carried out in a solvent which is inert under the reaction conditions, e.g. a halogenated hydrocarbon, xylene, or glacial acetic acid. The reaction may be carried out at an elevated temperature, e.g. from 20° to 150° C.

The cyclisation of process (f) may be carried out in a solvent which is inert under the reaction conditions, e.g. diethyl ether or benzene. The reaction may also, if desired, be carried out in the presence of a Lewis acid, e.g. boron trifluoride. The reaction is preferably carried out at a temperature of from 10° to 120° C. in presence of an organic base, e.g. piperidene.

Suitable solvents which are inert under the reaction conditions of process (g) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra- methyl- ammonium, anilinium, morpholinium and piperidinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphuric acid. As an alternative to the reaction conditions set out above, the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid.

In process (h) the anhydride is preferably a mixed anhydride of such a type that it will cleave preferentially, to give the desired chromone carboxamidotetrazole, as the major product when reacted with the 5-aminotetrazole. Examples of suitable acids from which the mixed anhydride may be derived are sulphonic acids e.g. benzene sulphonic acid, sterically hindered carboxylic acids, e.g. pivalic, isovaleric, diethylacetic or triphenylacetic acid, and alkoxy formic acids, e.g. a lower alkoxy formic acid such as ethoxy or isobutoxy formic acid. When an acid halide is used it may conveniently be an acid chloride. The reaction is preferably carried out under anhydrous conditions in a solvent which will not react with either the 5-aminotetrazole or the mixed anhydride or acid halide, e.g. pyridine or dimethylformamide. However when the reaction is carried out in a non-basic solvent, e.g. dimethylformamide, an adequate proportion of an acid acceptor, e.g. triethylamine, should also preferably be present. The reaction is preferably carried out at a temperature of from about $-15°$ to $+20°$ C. When an ester is used we prefer to use a lower alkoxy ester and to carry out the reaction in a solvent which is inert under the reaction conditions, e.g. glacial acetic acid, at a temperature of from about 100° to 150° C. When a compound of formula I in which E is $-COOH$ is used as starting material the reaction may be carried out by heating the compound of formula I and the 5-aminotetrazole in a solvent which is inert under the reaction conditions, e.g. dimethylacetamide, at a temperature of from 100° to 200° C. Alternatively the reaction may be carried out in the presence of a condensation agent, e.g. N,N'-carbonyl-diimidazole or dicyclohexyl carbodiimide, in an aprotic solvent, e.g. dimethylformamide, at a temperature of from about 10° to 40° C.

The starting materials for process (b) may be made by reacting a compound of formula IX,

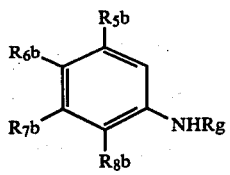

in which Rg, R$_5$b, R$_6$b, R$_7$b and R$_8$b are as defined above, with a compound of formula X,

Da—C≡C—Da    X in which Da is an ester group, to produce a mixture of compounds of formulae XI and XII,

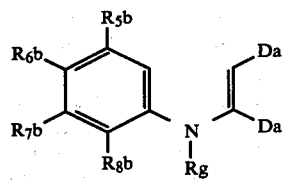

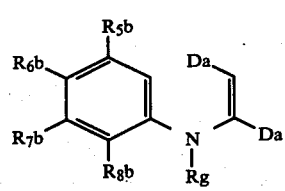

in which Rg, Da, R$_5$b, R$_6$b, R$_7$b and R$_8$b are as defined above.

The compounds of formula XI and XII may be hydrolysed to give compounds of formulae IV and III. Alternatively the groups Da in the compounds of formulae XI and XII may be converted using conventional techniques known per se, to other groups D and the resulting comounds cyclised, using the same conditions as for process (b) above, to yield a compound of formula II. As a further and preferred alternative the compounds of formula XI and XII may by cyclised, using the same conditions as for process (b) above, to give a compound of formula II in which D is an ester group, and the resulting compound of formula II is used itself in process (a), or the D group converted to another group D, e.g. an acid halide, amide or nitrile group, using techniques known per se.

The fumarate isomer of formula XII (or the corresponding compound in which Da has been converted to D) is the only isomer which can cyclise to give the required compounds of formula II. The proportion of the two isomers may be readily determined by nuclear magnetic resonnance spectroscopy and we have found that, in general, the desired fumaric acid derivative is only a minor proportion of the mixture of isomers obtained from the reaction.

The compounds of formula V, in which an adjacent pair of R$_5$c, R$_6$c, R$_7$c and R$_8$c represent the groups —COCH$_2$COCR" and —OM or halogen, may be made by reacting a compound of formula XIII,

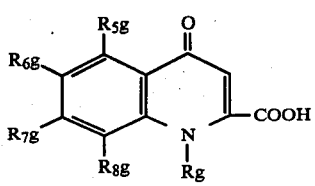

or an ester thereof,
in which Rg is as defined above,
and R$_5$g, R$_6$g, R$_7$g and R$_8$g have the same significances as R$_5$, R$_6$, R$_7$ and R$_8$ above, save that an adjacent pair of R$_5$g, R$_6$g, R$_7$g and R$_8$g, instead of forming a —COCH=CH(COOH)—O— chain, represent the groups —COCH$_3$ and —OM or halogen, in which M is as defined above,
with a compound of formula XIV,

R'CZ—CZR"    XIV in which R" is as defined above,
R' is a suitable leaving group, e.g. an alkoxy, halo, amino, alkylamino, substituted amino (e.g. an arylsulphonylamino group) or substituted alkylamino group, reactive with the carbanion of the —COCH$_3$ group of the compound of formula XIII, and
each Z is a carbonyl oxygen atom, or one Z may represent two halogen atoms and the other a carbonyl oxygen atom,
and if necessary hydrolysing the resulting compound to a compound of formula V. The preferred comounds of formula XIV are dialkyl oxalates, e.g. diethyl oxalate.

Compounds of formula V bearing a —COCH=C(COOH)—NL$_1$L$_2$ group, or a derivative thereof, may be made from known compounds in one or more steps using processes known per se.

The compounds of formula II may be made as described above or by a process analogous to process (c)(i).

Alternatively the compounds of formula II may, for example in the case of the acid halide, the amide and the nitrile, be made from comounds of formula I using conventional techniques, e.g. reaction of an ester of the compound of formula I with ammonia to produce the amide, followed by dehydration of the amide to form the nitrile.

The compounds of formula V carrying substituents —H and —O—C(COR")=CH—COR" may be made by reacting a compound of formula XV,

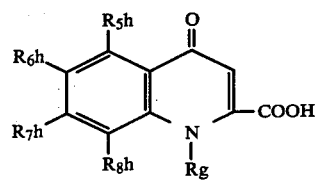

or an ester thereof,
in which Rg is as defined above, and R$_5$h, R$_6$h, R$_7$h and R$_8$h have the same significances as R$_5$, R$_6$, R$_7$ and R$_8$ above, save that an adjacent pair of R$_5$h, R$_6$h, R$_7$h and R$_8$h, instead of forming a —COCH=C(COOH)—O— chain, represent the groups —H and —OH, with a dialkyl acetylene dicarboxylate, in conventional manner, followed if necessary by hydrolysis of the reaction product.

Compounds of formula VIII may be made by reacting a compound of formula XVI,

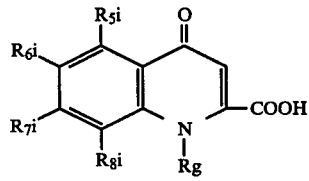

XVI or an ester thereof,
in which Rg is as defined above,
$R_{5i}$, $R_{6i}$, $R_{7i}$ and $R_{8i}$ have the same significances as $R_5$, $R_6$, $R_7$ and $R_8$ above, save that an adjacent pair of $R_{5i}$, $R_{6i}$, $R_{7i}$ and $R_{8i}$, instead of forming a chain —COCH=C(COOH)—O—, represent the pair of groups —OH and —COO—Alkyl,
with a methyl alkyl sulphoxide anion, e.g. the anion of dimethyl sulphoxide,
and reacting the resulting o-hydroxy-2-alkylsulphinyl compound with glyoxalic acid or an ester thereof.

The compounds of formula I in which E is —CN may be made by dehydrating the corresponding pyranoquinoline amide using, for example, phosphorus oxychloride, as dehydrating agent. The reaction is preferably carried out using at least one molar equivalent of dehydrating agent per mole of the pyranoquinolinone amide. Where the dehydrating agent reacts with one of $R_5$, $R_6$, $R_7$ or $R_8$ (e.g. a substituent comprising an —CH group) sufficient dehydrating agent should be used to satisfy the side reaction as well as the main reaction. The reaction may, if desired, be carried out in the presence of an acid binding agent, e.g. triethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C. depending on the dehydrating agent used. When phoshorus oxychloride is used a temperature of from 0° to 100° C. is preferred.

The chromone amide starting materials may be made by reacting a corresponding pyranoquinolinone ester with ammonia, using techniques conventional in the production of amides from esters, e.g. using an alkanol as solvent at a temperature of 0° to 120° C.

Compounds of formulae VI, VII, IX, XIII, XIV, XV and XVI are either known or may be made from known compounds using conventional techniques known per se.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable salts, and when E is a —COOH group, esters and amides of the 2-carboxylic acid group. Suitable salts include ammonium, alkali metal (e.g sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g hydroxy substituted alkylamines such as tris(hydroxymethyl)methylamine, or with simple monocyclic nitrogen heterocyclic compounds, e.g piperidine or morpholine. Suitable esters include simple lower alkyl esters, e.g the ethyl ester, esters derived from alcohols containing basic groups, e.g di-lower alkyl amino substituted alkanols such as the β-(diethylamino)-ethyl ester, and acyloxy alkyl esters, e.g a lower acyloxy-lower alkyl ester such as the pivaloyloxymethyl ester, or a bis-ester derived from a di-hydroxy compound, e.g a di(hydroxy-lower alkyl)ether, e.g the bis-2-oxapropan-1,3-diyl ester. The pharmaceutically acceptable acid addition salts of the basic esters, and also of those compounds in which one of $R_5$, $R_6$, $R_7$ and $R_8$ is a group —$NR_1R_2$, e.g the hydrochloride, the hydrobromide, the oxalate, the maleate or the fumarate salts, may also be used. The esters may be made by conventional techniques, e.g esterification or transesterification. The amides may be, for example, unsubstituted or mono- or di- C 1 to 6 alkyl amides and may be made by conventional techniques, e.g reaction of an ester of the corresponding acid with ammonia or an appropriate amine.

The compounds of formula I and pharmaceutically acceptable derivatives thereof are useful because they possess pharmacological activity in animals; in particular they are useful because they inhibit the release and-/or action of pharmacological mediators which result from the in vivo combination of certain types of antibody and specific antigen, e.g the combination of reaginic antibody with specific antigen (see Example 27 of British Patent Specification No. 1,292,601). The new compounds have also been found to interfere with reflex pathways in experimental animals and man and in particular those reflexes associated with lung function. In man, both subjective and objective changes which result from the inhalation of specific antigen by sensitised subjects are inhibited by prior administration of the new compounds. Thus the new compounds are indicated for use in the treatment of reversable airway obstruction and/or to prevent the secretion of excess mucous. The new compounds are thus indicated for the treatment of allergic asthma, so-called 'intrinsic' asthma (in which no sensitivity to extrinsic antigen can be demonstrated), bronchitis, coughs and the nasal and bronchial obstructions associated with the common colds. The new compounds may also be of value in the treatment of other conditions in which antigen-antibody reactions or excess mucous secretion are responsible for, or are an adjunct to, disease, for example, hay fever; certain eye conditions, e.g trachoma; alimentary allergy, e.g urticaria and atopic eczema; and gastrointestinal conditions, for example gastrointestinal allergy, especially in children, e.g milk allergy, or ulcerative colitis.

For the above mentioned uses the dosage administered will, of course, vary with the compound employed, the mode of administration and the treatment desired. However, in general, satisfactory results are obtained when the compounds are administered at a dosage of from 0.001 to 50 mg per kg of animal body weight in the test set out in Example 27 of British Patent Specification No. 1,292,601. For man the indicated total daily dosage is in the range of from 0.01 mg to 1,000 mg preferably from 0.01 mg to 200 mg and more preferably from 1 mg to 60 mg, which may be administered in divided doses from 1 to 6 times a day or in sustained release form. Thus unit dosage forms suitable for administration (by inhalation or oesophageally) comprise from 0.01 mg to 50 mg, preferably 0.01 mg to 20 mg and more preferably from 0.01 mg to 10 mg of the compound preferably admixed with a solid or liquid pharmaceutically acceptable diluent, carrier or adjuvant.

The compounds of formula I, and pharmaceutically acceptable derivatives thereof, have the advantage that they are more efficacious in certain pharmacological models, or are longer acting than compounds of similar structure to the compounds of formula I. Furthermore the compounds of formula I, and pharmaceutically acceptable derivatives thereof, are advantageous in that they are more efficaceous in interfering with reflex pathways and in inhibiting the secretion of mucous than are compounds of similar structure to the compounds of formula I.

We prefer each of $R_g$, $R_5$, $R_6$, $R_7$ and $R_8$, when they contain carbon, to contain up to 8, and preferably up to 4 carbon atoms. Specifically we prefer $R_5$, $R_6$, $R_7$ and $R_8$ to be selected from hydrogen, methoxy, propyl, allyl, methyl, ethyl, chlorine, bromine and hydroxy. The —COCH=CE—O— chain may be bonded to the benzene ring in any sense and in any of the adjacent positions $R_5$, $R_6$, $R_7$, $R_8$. However, we prefer the chain to be bonded in the positions $R_6$ and $R_7$ the —O— part of the chain being in position $R_7$. We also prefer the group E to be a —COOH group.

According to the invention there is also provided a process for the production of a pharmaceutically acceptable salt of a compound of formula I, which comprises treating a compound of formula Ic,

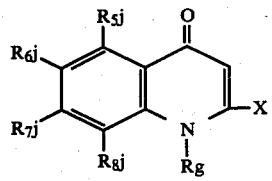

in which $R_g$ is as defined above,
$R_{5j}$, $R_{6j}$, $R_{7j}$ and $R_{8j}$ have the same significances as $R_5$, $R_6$, $R_7$ and $R_8$ above, save that an adjacent pair of $R_{5j}$, $R_{6j}$, $R_{7j}$ and $R_{8j}$ may form a chain —O—C(X)=CHCO—, and
X is a 5-tetrazolyl group, an (N-tetrazol-5-yl)carboxamido group, a carboxylic acid group (or an ester thereof, or another salt thereof), a nitrile group, an acid halide group or an amide group,
with a compound containing an available pharmaceutically acceptable cation and capable of converting the group X to a pharmaceutically acceptable salt of an E group.

Compounds capable of converting the group X to a pharmaceutically acceptable salt of an E group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I with an appropriate base, e.g with an alkaline-earth or alkali metal hydroxide, carbonate or bicarbonate in aqueous solution or by a metathetical process with an appropriate salt. When a strongly basic compound is used care should be taken, e.g by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g by freeze drying.

According to our invention we also provide a pharmaceutical composition comprising (preferably less than 80%, and more preferably less than 50% by weight) of a compound of formula I, or a pharmaceutically acceptable derivative thereof, in combination with a pharmaceutically acceptable adjuvant, diluent or carrier. Examples of suitable adjuvants, diluents or carriers are:- for tablets capsules and dragées; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable derivative thereof, preferably is in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gastrointestinal tract.

The 5-tetrazolyl and (N-tetrazol-5-yl)carboxamido groups are of formulae XVII and XVIII respectively,

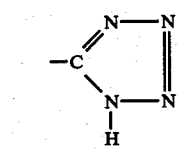

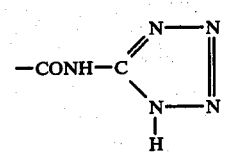

The groups of formulae XVII and XVIII may exist in tautomeric forms and such tautomeric forms are included within the definition of the compounds of formula I.

The invention is illustrated, but in no way limited by the following Examples.

EXAMPLE 1

4,6-Dioxo-10-propyl-4H,6H-pyrano[3,2-g]quinoline-2,8-dicarboxylic acid (a) 4-Acetamido-2-allyloxyacetophenone 4-Acetamido-2-hydroxyacetophenone (19.3 g) allyl bromide (12.1 ml) and anhydrous potassium carbonate (21.5 g) were stirred in dry dimethylformamide (250 ml) at room temperature for 24 hours. The reaction mixture was poured into water and the product was extracted with ethyl acetate. The organic solution was then washed well with water dried over magnesium sulphate and evaporated to dryness. The sub-title product was obtained as buff coloured solid (20.5 g). The structure of the product was confirmed by NMR and mass spectroscopy.

(b) 4-Acetamido-3-allyl-2-hydroxyacetophenone

The above allyl ether (18.4 g) was heated at 200°–210° C. for 4 hours. 17.1 g of the thermally rearranged sub-title product was obtained as a brown solid. Again the structure was confirmed by NMR and mass spectroscopy.

(c) 4-Acetamido-2-hydroxy-3-propyl acetophenone

The product of step (b) (17 g) was dissolved in glacial acetic acid and hydrogenated in the presence of Adams catalyst until hydrogen uptake had ceased. The catalyst was filtered off through a kieselguhr filter and the filtrate was evaporated to leave 13.0 g of almost colourless solid. The mass and NMR spectra confirmed the structure of the product.

(d) Ethyl 7-acetamido-4-oxo-8-propyl-4H-1-benzopyran-2-carboxylate

A mixture of diethyl oxalate (19.3 g; 17.9 ml) and the above product of step (c) (12.4 g) in dry ethanol (100 ml) was added to a stirred solution of sodium ethoxide in ethanol (prepared by dissolving sodium (6.1 g) in dry ethanol (200 ml)). The reaction mixture was refluxed for 3 hours and then poured into dilute hydrochloric acid and chloroform. The chloroform layer was separated, washed with water and dried. The solvent was evaporated to leave a brown solid which was dissolved in ethanol (300 ml) containing concentrated hydrochloric acid (3 ml) and the whole was refluxed for 1 hour. The reaction mixture was poured into water and the product was extracted into ethyl acetate which was washed with water and dried. The solvent was evaporated to leave 10 g of a sticky solid which had mass and NMR spectra consistent with the expected product.

(e) Ethyl 7-amino-4-oxo-8-propyl-4H-1-benzopyran-2-carboxylate

A solution of the amide of step (d) (10 g) in ethanol (300 ml), containing concentrated hydrochloric acid (5 ml), was refluxed for 8 hours. The reaction mixture was diluted with water and extracted into ethyl acetate. The extract was washed with water, dried and the solvent was evaporated to leave a dark brown semisolid. This was chromatographed on a silica gel column, using ether as eluant to give 4.8 g of the required product whose structure was confirmed by mass and NMR spectral evidence; mp 84°–87° C.

(f) 8-Ethoxycarbonyl-2-methoxycarbonyl-4,6-dioxo-10-propyl-4H,6H-pyrano[3,2-g]quinoline The amino benzopyran of step (e) (2.0 g) and dimethyl acetylene dicarboxylate (1.24 g; 1.01 ml) were refluxed in ethanol (30 ml) for 26 hours. The reaction mixture was cooled to 0° C. and the insoluble yellow-brown solid was collected by filtration and washed with a little ethanol and dried to give 2.0 g of a product which was a mixture of maleic and fumaric esters obtained by Michael addition of the amine to the acetylene.

This mixture of esters (2.0 g) was treated with polyphosphoric acid (30 ml) and heated on the steam bath with stirring for 20 minutes. The reaction mixture was then poured onto ice and stirred with ethyl acetate. The organic layer was separated, washed with water and dried. The solvent was evaporated to leave 1.6 g of a yellow orange solid. Recrystallisation of this solid from ethyl acetate gave the required product as fluffy orange needles mp 187°–188° C.

Analysis Found: C, 62.0%; H, 5.1%; H, 3.7%: $C_{20}H_{19}NO_7$ Required: C 62.3%; H, 4.9%; N, 3.6%.

(g) 4,6-Dioxo-10-propyl-4H,6H-pyrano[3,2-g]quinoline-2,8-dicarboxylic acid

The above bis ester (2.5 g) was refluxed with sodium bicarbonate (1.64 g) in ethanol (100 ml) and water (50 ml) for 1½ hours. The whole was poured into water and acidified to precipitate a gelatinous solid. This was collected by filtration, refluxed with ethanol and the product was separated by centrifugation (1.4 g) mp 303°–304° C. dec. The structure of the product was confirmed by mass and NMR evidence.

(h) Disodium 4,6-dioxo-10-propyl-4H,6H-pyrano[3,2-g]quinoline-2,8-dicarboxylate

The bis acid from step (g) (1.35 g) and sodium bicarbonate (0.661 g) in water (150 ml) were warmed and stirred until a clear solution was obtained. This solution was filtered and the filtrate was freeze dried to give 1.43 g of the required disodium salt.

Analysis Found: C, 46.1%; H, 4.0%; N, 2.9%: $C_{17}H_{11}NO_7Na_2$ 12.5% $H_2O$ required: C, 46.1%; H, 3.8%; N, 3.15%.

EXAMPLE 2

4,6-Dioxo-1-ethyl-10-propyl-4H,6H-pyrano[3,2-g]quinoline-2,8-dicarboxylic acid (a) 4-(N-Acetyl-N-ethyl)amino-2-allyloxyacetophenone 4-(N-acetyl-N-ethyl)amino-2-hydroxyacetophenone (92.6 g), allyl bromide (51 mls) and anhydrous potassium carbonate (90.4 g) were stirred in dry dimethylformamide (500 mls) for 17 hours. The reaction mixture was poured into water and the product was extracted with ether. The organic solution was then washed well with water, dried over magnesium sulphate and evaporated to dryness. The product was obtained as an oil (102.5 g). The structure of the product was confirmed by NMR and mass spectroscopy.

(b) 4-(N-Acetyl-N-ethyl)amino-3-propyl-2-hydroxyacetophenone

The allyl ether product of step (a) (100.5 g) was refluxed in diethylaniline (300 mls) for 3 hours. The reaction mixture was cooled and poured into dilute hydrochloric acid and extracted into ether, which latter was washed with dilute hydrochloric acid, and then with water. The organic solution was extracted with 10% sodium hydroxide solution which was then acidified. The precipitated product was extracted with ether which was dried over magnesium sulphate. The resulting ethereal solution was evaporated to dryness to give a yellow-brown oil (78.7 g). This oil was a mixture of 4-(N-acetyl-N-ethyl)amino-3-allyl-2-hydroxyacetophenone and 6-(N-acetyl-N-ethyl)amino-3-allyl-2-hydroxyacetophenone.

This mixture was dissolved in ethanol (500 mls) and glacial acetic acid (20 mls) and hydrogenated in the presence of Adams catalyst until hydrogen uptake had ceased. The catalyst was filtered off through kieselguhr and the filtrate evaporated to leave 79.9 g of brown oil. This brown oil was a mixture and was separated by high pressure liquid chromatography using ether/petroleum ether (1:1) as solvent to give 44.2 g of the sub-title compound and 23.8 g of 6-(N-acetyl-N-ethyl)amino-3-propyl-2-hydroxyacetophenone.

(c) 4-N-Ethylamino-3-propyl-2-hydroxyacetophenone 4-(N-Acetyl-N-ethyl)amino-3-propyl-2-hydroxyacetophenone (44 g) was refluxed in 48% hydrogen bromide in glacial acetic acid (100 mls), glacial acetic acid (500 mls) and water (20 mls) for 6 hours. The reaction mixture was poured on to ice-water and extracted with ethyl acetate which was washed with water, sodium bicarbonate solution, then water again and dried over magnesium sulphate. The organic solvent was evaporated to dryness to leave the sub-title compound as a red oil (34 g). The structure was confirmed by NMR and mass spectroscopy.

(d) Methyl 6-acetyl-1-ethyl-7-hydroxy-4-oxo-8-propyl-4H-quinoline-2-carboxylate

The amine product of step (c) (17 g) and dimethacetylenedicarboxylate (11.3 mls) were refluxed in ethanol (300 mls) for 17 hrs. The reaction mixture was cooled and evaporated to dryness to leave a deep red oil. This oil was chromatographed on a silica gel column using ether/petroleum ether (1:1) as eluant to give 19.1 g of dimethyl 1-(4-acetyl-3-hydroxy-2-propylphenyl)-N-ethylaminomaleate m.p. 83°–87° C.

The maleic ester (5 g) was heated and stirred in polyphosphoric acid (100 mls) on the steam bath for 10 minutes. The reaction mixture was cooled and poured on to a mixture of ice-water and ethyl acetate. The organic solution was separated, washed with water and dried over magnesium sulphate. The solvent was evaporated to dryness to leave a pale yellow solid. This product was purified by high pressure liquid chromatography to give 2.6 g of the sub title compound m.p. 121°–123° C.

Analysis Found: C: 65.5%; H: 6.6%; N; 4.2%: $C_{18}H_2NO_5$ Required: C: 65.3%; H; 6.34%; N; 4.23%.

Methyl 6-acetyl-1-ethyl-5-hydroxy-4-oxo-4H-quinoline-2-carboxylate was obtained from the purification as a pale yellow solid (100 mgs).

(e) Diethyl 4,6-dioxo-1-ethyl-10-propyl-4H-6H-pyrano[3,2-g]quinoline-2,8-dicarboxylate The hydroxy ketone product of step (d) (1.0 g) and diethyl oxalate (3.3 mls) in dry dimethylformamide (25 mls) were added to ether washed 50% sodium hydride (0.581 g) in dry dimethylformamide (20 mls) and the reaction mixture stirred for 4 hours. The reaction mixture was then poured into water, acidified and extracted with ethyl acetate, which was then washed with water and dried over magnesium sulphate. The solvent was evaporated to dryness to give an oil which was dissolved in ethanol (100 mls) and concentrated hydrochloric acid (a few drops) added. The solution was refluxed for ½ hr, cooled, poured into water and extracted with ethyl acetate, which was washed with water and dried over magnesium sulphate. The solvent was evaporated to dryness to leave an oil which solidified on trituration with 40°–60° petroleum ether (1.2 g). The structure of the compound was confirmed by NMR.

(f) 4,6-Dioxo-1-ethyl-10-propyl-4H,6H-pyrano[3,2-g]quinoline-2,8-dicarboxylic acid The above bis ester (1.0 g) and sodium bicarbonate (0.787 g) in ethanol (85 mls) and water (32 mls) were refluxed for 4 hours. The reaction mixture was poured into water, acidified and the precipitate was collected by filtration and dried. The product was purified by triturating with boiling ethanol, then twice with boiling acetone. After each trituration the mixture was centrifuged and the supernatant liquid was removed by decantation. The residual solid was dried to give 0.547 g of the required di-acid as a yellow powder m.p. 298°–300° C. dec.

Analysis: Found: C: 61.3% H; 5.0% N; 3.6%: $C_{19}H_{17}NO_7$ Required: C: 61.5% H; 4.6% N; 3.79%.

(g) Disodium 4,6-Dioxo-1-ethyl-10-propyl-4H,6H-pyrano[3,2-g]quinoline-2,8-dicarboxylate The above di-acid (4.098 g), suspended in water (100 mls) and was treated with sodium bicarbonate (1.82 g). The resulting solution was filtered and the filtrate was treated with acetone until complete precipitation of the product had occurred. The required di-sodium salt was filtered off and dried to give 3.39 g of a pale yellow powder.

Analysis: Found: C: 51.1%; H; 4.3%; N; 3.0%: $C_{19}H_{15}MN_2O_7$ Required: C: 51.1%; H; 4.1%; N; 3.1% (6.9% water).

EXAMPLE 3

The following compounds may also be made by the processes described above:
(i) 5-Ethyl-4,8-dioxo-10-propyl-4H,8H-pyrano[2,3-h]quinoline-2,6-dicarboxylic acid
(ii) 4,10-Dioxo-4H,10H-pyrano[2,3-f]quinoline-2,8-dicarboxylic acid
(iii) 10-Bromo-4,6-dioxo-4H,6H-pyrano[3,2-g]quinoline-2,8-dicarboxylic acid
(iv) 5-Hydroxy-4,6-dioxo-10-propyl-4H,6H-pyrano[3,2-g]quinoline-2,8-dicarboxylic acid ;P1
(v) 4,9-Dioxo-4H,9H-pyrano[2,3-g]quinoline-2,7-dicarboxylic acid
(vi) 4,10-Dioxo-4H,10H-pyrano[2,3-f]quinoline-2,8-di[N-(tetrazol-5-yl)]carboxamide
(vii) 10-Bromo-4,6-dioxo-2,8-di-(tetrazol-5-yl)-4H,6H-pyrano[3,2-g]quinoline.

We claim:
1. A compound having the formula

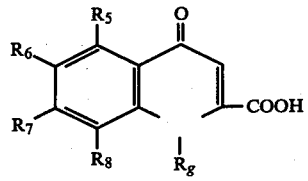

in which $R_6$ and $R_7$ form a chain —COCH=C(COOH)—O—, $R_5$ and $R_8$, which may be the same or different, are sterically compatible substituents selected from hydrogen and alkyl having up to 8 carbon atoms, and $R_g$ is hydrogen or alkyl having up to 8 carbon atoms, and pharmaceutically acceptable salts and ethyl esters thereof.

2. A compound according to claim 1, wherein each of $R_5$, $R_8$ and $R_g$, when they are alkyl, contain up to 4 carbon atoms.

3. A compound according to claim 1, wherein the —COCH=C(COOH)—O— chain is bonded with the —O— end thereof in position $R_7$.

4. A compound according to claim 1, wherein $R_5$ and $R_8$ are selected from hydrogen and propyl.

5. A compound according to claim 1, wherein $R_g$ is ethyl.

6. 4,6-Dioxo-1-ethyl-10-propyl-4H,6H-pyrano[3,2-g]quinoline-2,8-dicarboxylic acid or a pharmaceutically acceptable salt thereof.

7. 4,6-Dioxo-10-propyl-4H,6H-pyrano[3,2-g]quinoline-2,8-dicarboxylic acid or a pharmaceutically acceptable salt thereof.

8. A pharmaceutical composition suitable for the treatment of a condition involving an antibody antigen reaction or a reflex pathway comprising an effective amount of a compound according to claim 1 in combination with a pharmmaceutically acceptable adjuvant, diluent or carrier.

9. A composition according to claim 8 comprising less than 80% by weight of active ingredient.

10. A composition comprising from 0.01 mg to 50 mg of a compound according to claim 1, as active ingredient, in unit dosage form.

11. A method of treatment of a condition involving an antibody antigen reaction or a reflex pathway, which comprises administering an effective amount of a compound according to claim 1 to an animal suffering from such a condition.

* * * * *

UNITED STATES PATENT AND TRADEMARK OFFICE
CERTIFICATE OF CORRECTION

PATENT NO. :   4,474,787
DATED      :   October 2, 1984
INVENTOR(S) :  HUGH CAIRNS ET AL.

It is certified that error appears in the above-identified patent and that said Letters Patent is hereby corrected as shown below:

Column 5, line 36, "an an" should be --and an--.

Column 9, line 33, "-CH" should be -- -OH --.

Column 16, line 15, " $C_{19}H_{15}MN_2O_7$ ", should be $$--C_{19}H_{15}NNa_2O_2--.$$

Signed and Sealed this

Ninth Day of April 1985

[SEAL]

*Attest:*

DONALD J. QUIGG

*Attesting Officer*  *Acting Commissioner of Patents and Trademarks*

UNITED STATES PATENT AND TRADEMARK OFFICE
CERTIFICATE OF CORRECTION

PATENT NO. : 4,474,787
DATED : October 2, 1984
INVENTOR(S) : HUGH CAIRNS ET AL.

It is certified that error appears in the above-identified patent and that said Letters Patent is hereby corrected as shown below:

Column 16, line 37-44, claim 1, the structural formula should be as follows:

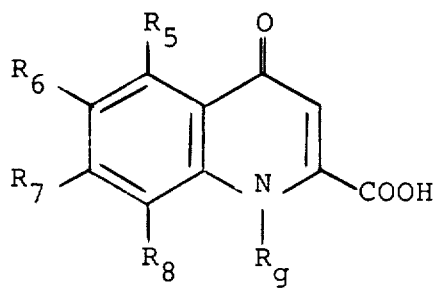

Signed and Sealed this

Second Day of November, 1993

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.:     4,474,787

DATED:          October 2, 1984

INVENTORS:      Hugh Cairns et al.

PATENT OWNER:   Fisons plc

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

5 YEARS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
  Commissioner of Patents and Trademarks